United States Patent [19]
Mehlberg

[11] Patent Number: 5,817,908
[45] Date of Patent: Oct. 6, 1998

[54] STAGED ALKYLATION PROCESS

[75] Inventor: Robert L. Mehlberg, Wheaton, Ill.

[73] Assignee: Amoco Corporation, Chicago, Ill.

[21] Appl. No.: 650,637

[22] Filed: May 20, 1996

[51] Int. Cl.$^6$ .................................. C07C 2/56; C07C 2/58
[52] U.S. Cl. .......................... 585/716; 585/721; 585/731; 585/730
[58] Field of Search ...................................... 585/709, 716, 585/730, 731, 721, 446, 449, 458, 462, 323, 331

[56] References Cited

U.S. PATENT DOCUMENTS

| | | | |
|---|---|---|---|
| 3,887,635 | 6/1975 | Parker et al. | 260/683.47 |
| 5,073,653 | 12/1991 | Butler | 585/449 |
| 5,220,095 | 6/1993 | Hommeltoft et al. | 585/720 |
| 5,245,100 | 9/1993 | Hommeltoft et al. | 585/730 |
| 5,396,017 | 3/1995 | Hommeltoft | 585/724 |
| 5,396,018 | 3/1995 | Hommeltoft | 585/724 |
| 5,414,187 | 5/1995 | King et al. | 585/730 |

FOREIGN PATENT DOCUMENTS

| | | | |
|---|---|---|---|
| 0 433 954 A1 | 6/1991 | European Pat. Off. | C07C 2/62 |
| 0 638 532 A1 | 2/1995 | European Pat. Off. | C07C 2/62 |
| 0 663 377 A1 | 7/1995 | European Pat. Off. | C07C 2/62 |
| 0 714 871 A1 | 6/1996 | European Pat. Off. | C07C 2/62 |
| 0 790 224 A1 | 8/1997 | European Pat. Off. | C07C 2/54 |
| 865161 | 5/1941 | France . | |

*Primary Examiner*—Helane Myers
*Assistant Examiner*—In Suk Bullock
*Attorney, Agent, or Firm*—Richard A. Kretchmer; Frank J. Sroka

[57] ABSTRACT

A staged alkylation process in the presence of an acid catalyst in a fixed bed of particulate contact material in an alkylation reactor is disclosed.

16 Claims, 1 Drawing Sheet

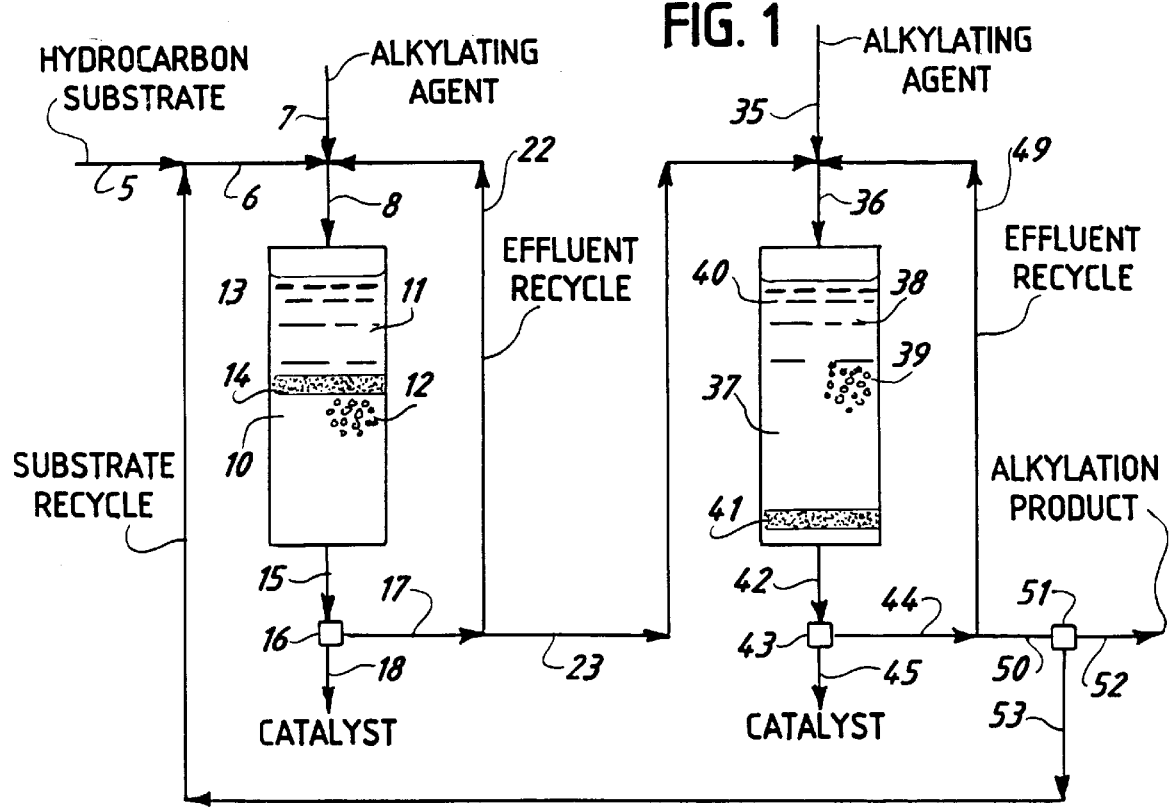
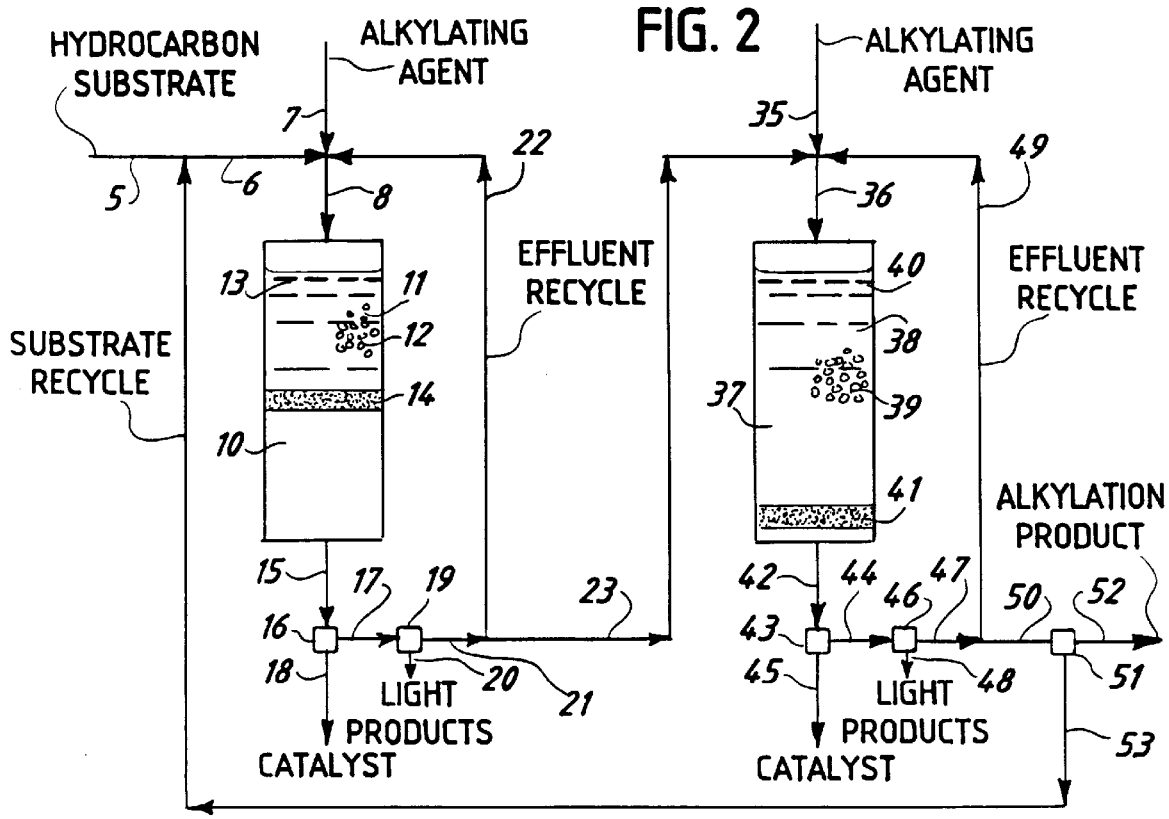

STAGED ALKYLATION PROCESS

BACKGROUND OF THE INVENTION

1. Field of the Invention

The present invention relates to a process for the liquid phase alkylation of a hydrocarbon substrate with an olefinic alkylating agent in the presence of a solid acid alkylation catalyst, and more particularly concerns an aforesaid alkylation process in the presence of an acid catalyst in a fixed bed of particulate contact material in an alkylation reactor.

2. Discussion of the Prior Art

The olefinic alkylating agents typically employed in the liquid-phase alkylation of a hydrocarbon substrate in the presence of an alkylation catalyst may also be polymerized by contact with the alkylation catalyst. Such competing polymerization reactions occur more readily than do the desired alkylation reaction between the olefinic alkylating agent and the hydrocarbon substrate. In addition, other undesirable side or secondary reactions involving the alkylating agent and/or an alkylation product may also occur under the alkylation conditions employed.

A conventional procedure to inhibit and minimize the occurrence of concurrent polymerization reactions and any other undesirable side or secondary reactions is to effect the catalytic alkylation reaction under conditions that are designed to avoid intimate contact of the olefinic alkylating agent and the alkylation products with the catalyst material in the comparative absence of the hydrocarbon substrate. To accomplish this, it has been customary to provide a substantial excess of the hydrocarbon substrate over both the alkylating agent and the alkylation products in the reaction mixture in the reaction zone. For example, the alkylating reaction has been introduced in successive increments in a continuous series of reaction zones or stages containing hydrocarbon substrate already in contact with the catalyst.

However, under such procedures, it is frequently difficult to adequately control the quantities of the various materials introduced, or their relative proportions in any stage, and also the degree of mixing which is accomplished from stage to stage. As a result, there may be areas in any particular zone or stage in which the alkylating agent may come in contact with substantially free catalyst materials to produce the undesired polymerization or other side reactions, and thereby to reduce the yield of alkylation products.

Furthermore, the aforesaid liquid-phase alkylation is highly exothermic. In order to maintain the reaction temperature sufficiently low to enhance the occurrence of the desired alkylation reaction and the production of high octane alkylation products over the competing concurrent polymerization reactions and other side or secondary reactions, the reaction pressure is maintained at a level such that sufficient vaporization occurs and the resulting vapor is withdrawn from the reactor, to remove the heat of reaction and thereby cool the reaction mixture.

The aforesaid problems of minimizing contact of the alkylating agent and alkylation products with the alkylation catalyst and of removal of exothermal heat from the alkylation reaction zone are greatly exacerbated in an alkylation reaction system in which the alkylation catalyst is adsorbed on a confined volume of particulate contact material within a fixed bed within a reactor and in which this confined volume constitutes the reaction zone and moves from one end to the other end of the reactor and in which there is no vapor phase and no possibility of evaporative cooling within the reactor.

Hommeltoft and Topsoe U.S. Pat. Nos. 5,220,095 and 5,245,100 and Hommeltoft, U.S. Pat. Nos. 5,396,017 and 5,396,018, disclose such an alkylation system for the liquid phase alkylation of an isoparaffin with an olefinic alkylating agent, which comprises passing a process stream of the isoparaffin and alkylating agent under alkylation conditions through a fixed bed alkylation reactor of particulate polar contact material in the presence of a fluorinated sulfonic acid catalyst. The fluorinated sulfonic acid is adsorbed on a confined area of the polar contact material, which area constitutes the reaction zone. When the process stream is passed in one flow direction through the reactor, the reaction zone in the form of the catalyst adsorbed on the contact material migrates on the contact material in the direction of the flow of the process stream. Thus, during the alkylation reaction, the acid catalyst and consequently the reaction zone moves to a new position in the fixed bed located nearer the outlet end of the alkylation reactor, as a result of interaction with the process stream flowing through and reacting in the reaction zone. The migration speed of the acid catalyst on the contact material in the fixed bed in the reactor is much lower than the migration speed of the hydrocarbons in the process and product stream resulting in a very long elution time for the acid catalyst relative to the elution time for the hydrocarbons in the process and product streams.

In one embodiment disclosed in aforesaid U.S. Pat. No. 5,220,095, when the reaction zone approaches the outlet end of the alkylation reactor, the flow direction of the process stream through the fixed bed in the alkylation reactor is reversed to thereby cause the reaction zone to reverse its direction of movement in the fixed bed and to move nearer the opposite end of the alkylation reactor by interaction with the process stream as described above. It is thus possible to reuse the acid catalyst without recovering the acid.

In another embodiment disclosed in aforesaid U.S. Pat. No. 5,245,100, having reached the outlet end of a first reactor, the acid catalyst elutes from the fixed bed in the first reactor and is transferred together with the product stream to the inlet end of a second reactor which also contains a fixed bed of a polar contact material. The acid catalyst is then adsorbed within a confined area of the contact material in the fixed bed within the second reactor and processed therein as in the first reactor. When the acid catalyst elutes from the fixed bed in the second reactor and passes out of the outlet of the second reactor, it is recycled to the inlet end of the first reactor.

There are other disclosures of alkylation processes that employ halogenated sulfonic acid as an alkylation catalyst. King et al., U.S. Pat. No. 5,414,187, discloses a process for the alkylation of an isoalkane with an olefin in the presence of a catalyst complex comprising an organosulfonic acid having at least one covalent carbon-fluorine bond or one carbon-phosphorus bond provided by a phosphono radical and a Lewis acid. The aforesaid organosulfonic acid may be impregnated onto a substantially inert support and employed as a supported acid catalyst in the alkylation process. In addition, Parker et al., U.S. Pat. No. 3,887,635, discloses a process for the alkylation of an isoparaffin with an olefin in the presence of a catalyst formed from a strong halosulfuric acid or halosulfonic acid, such as trihalomethanesulfonic acid, or mixtures thereof, and a catalyst moderator. This acid catalyst can also be incorporated with a substantially inert solid carrier or support and used as such in a fixed bed, moving bed or fluid bed reaction zone.

Thus far, no one has disclosed a process for minimizing contact of the alkylating agent and alkylation products with the alkylation catalyst or of controlling the reaction temperature and exothermal heat in the reaction zone in the alkylation system of Hommeltoft and Topsoe. Furthermore, as a result of the desirability in certain instances to use two or more alkylating agents and to form two or more alkylation products, it would also be highly desirable to have the facility to optimize the alkylation conditions for each set of alkylating agent and alkylation product in the aforesaid alkylation system of Hommeltoft and Topsoe.

OBJECTS OF THE INVENTION

It is therefore a general object of the present invention to provide an improved aforesaid alkylation method involving an alkylation catalyst on the surface of particulate contact material within a confined volume in a fixed bed of the particulate contact material and that affords the aforesaid desirable features and overcomes the aforesaid problems.

More particularly, it is an object of the present invention to provide an improved aforesaid method that enhances the occurrence of the desired alkylation reaction and minimizes the occurrence of any competing polymerization reactions or other undesirable side or secondary reactions.

It is a further object of the present invention to provide an improved aforesaid method that permits a reduction in the exothermic heat generated in the alkylation reaction zone.

It is another object of the present invention to provide an improved aforesaid method that facilitates the use of different alkylation conditions simultaneously in the same alkylation system.

Other objects and advantages of the present invention will become apparent upon reading the following detailed description and appended claims.

SUMMARY OF THE INVENTION

These objects are achieved by the process of the present invention which is an improvement in a process for the liquid phase alkylation of a hydrocarbon substrate with an olefinic alkylating agent in the presence of a halogenated sulfuric acid or halogenated sulfonic acid catalyst in a fixed bed of particulate contact material in an alkylation reactor, comprising the steps of establishing on the contact material a reaction zone of the aforesaid acid catalyst adsorbed on a confined volume of the contact material within the fixed bed, passing a process stream of the hydrocarbon substrate and alkylating agent at alkylation conditions in one flow direction through the reactor, with the acid catalyst and reaction zone migrating on the contact material in the fixed bed in the direction of flow of the process stream and at a lower superficial velocity than the superficial velocity of the process stream and product stream comprising alkylated products and unreacted hydrocarbon substrate, and withdrawing the product stream from the reactor. The improvement comprises: (a) staging the alkylation reaction by conducting the alkylation in x alkylation reactors in series, wherein x is from 2 to 20, and introducing into each such reactor a fraction of 1/x±up to 0.3 of the total amount of at least one alkylating agent employed, with the fraction introduced into one such reactor being the same as or different from the fraction introduced into any other such reactor in the series, with the contact material and catalyst employed in one such reactor being the same as or different from the contact material and catalyst, respectively, employed in any other such reactor, and with the alkylating agent and alkylation conditions employed in one such reactor being the same as or different from the alkylating agent and alkylation conditions, respectively, employed in any other such reactor; (b) establishing on the contact material within the fixed bed in each such alkylation reactor a reaction zone with the acid catalyst adsorbed on a confined volume of such contact material; (c) passing a process stream of aforesaid hydrocarbon substrate and an aforesaid fraction of aforesaid at least one alkylating agent at alkylation conditions in one flow direction through the first aforesaid alkylation reactor; (d) withdrawing a product stream comprising alkylation products and unreacted hydrocarbon substrate from the first alkylation reactor; (e) introducing into the next alkylation reactor in the series a process stream comprising at least a portion of the product stream of alkylation products and unreacted hydrocarbon substrate withdrawn from the preceding alkylation reactor in the series and another aforesaid fraction of aforesaid at least one alkylating agent, passing such process stream at alkylation conditions in one flow direction through such next alkylation reactor in the series, and withdrawing a product stream of alkylation products and unreacted hydrocarbon substrate from such next alkylation reactor; and (f) if x is greater than 2, repeating step (e) for each successive alkylation reactor in the series.

BRIEF DESCRIPTION OF THE DRAWINGS

FIG. 1 is a schematic illustration of one embodiment of the method of this invention involving two alkylation reactors in series in which the product stream from the first reactor is split into (1) a first stream which is combined with additional alkylating agent and introduced into the second reactor, and (2) a second stream which is recycled to the first reactor. The product stream from the second reactor is split to form (1) a first stream which is recycled to the second reactor, and (2) a second stream which is split again to form a stream which is recycled to the first reactor and a product stream which is recovered.

FIG. 2 is a schematic illustration of a second embodiment of the method of this invention which is a modification of the embodiment of FIG. 1 in which light components are removed from the product streams from each of the two reactors before each product stream is split.

DETAILED DESCRIPTION OF THE PREFERRED EMBODIMENTS

Suitable hydrocarbon substrates for use in the method of this invention include straight and/or branched chain $C_2$ to $C_{10}$ paraffins such as butane, hexane and the like, preferably $C_4$ to $C_6$ isoparaffins such as isobutane, isopentane and isohexane. Volatile aromatic compounds can also be employed as the hydrocarbon substrate in the method of this invention. Suitable volatile aromatic compounds comprise at least one of benzene, toluene and thiophene and preferably comprise both benzene, toluene. The source of the aforesaid suitable hydrocarbon substrates is not limited to any particular refinery stream or gasoline blending stock, and the exact composition of the source refinery stream or blending stock will depend on its source.

Suitable olefinic alkylation agents include $C_2$ to $C_{12}$ terminal and internal monoolefins such as ethylene, propylene, isobutylene, butene-1, butene-2, trimethylethylene, the isomeric pentenes and similar higher monoolefinic hydrocarbons of either a straight chain or a branched chain structure. Preferably, the $C_2$ to $C_6$ monoolefins are used, although the highly-branched $C_7$ to $C_{12}$ monoolefins may also be used. Cycloolefins may also be used. The reaction mixtures may also contain small amounts of diolefins. Although it is desirable from an economic standpoint to use the normally gaseous olefins as reactants, normally liquid olefins may also be used. Thus, the method of the present invention contemplates the use of reactable dimers and trimers and the like of the above-mentioned olefins, such as, for example, the diisobutylene and triisobutylene dimers and trimers, the codimer of normal butylene and isobutylene, of butadiene and isobutylene, and the like. Mixtures of two or more of the olefins above described can also be used as the alkylating agent.

The alkylation catalyst employed in the method of the present invention is a halogenated sulfuric or halogenated sulfonic acid. Thus, suitable acid catalysts for use in the method of the present invention include fluorinated sulfonic acids such as fluorinated alkane sulfonic acids, in particular, $C_1$ to $C_4$ perfluorinated alkanesulfonic acids. The acid catalyst typically employed is fluorosulfonic acid, trifluoromethanesulfonic acid or trifluoroethanesulfonic acid, and preferably is trifluoromethanesulfonic acid.

Also suitable for use as the alkylation catalyst in the method of this invention is the class of organosulfonic acids and acid derivatives whose compositions and preparations are described in King et al., U.S. Pat. No. 5,414,187, and were originally described in PCT application WO 90/07480, which was published on Jul. 12, 1990. Such acids have at least one covalent carbon-fluorine bond and at least one covalent carbon-phosphorus bond provided by a phosphono radical to increase the acidity of the organosulfonic acid and a Lewis acid complexed with at least a portion of the sulfonic acid groups.

In one embodiment, the organosulfonic acid comprises one or more fluorine atoms, sulfo radicals and phosphono radicals, each such radical being bonded to the same or different carbon atom, with the proviso that at least one sulfo radical and at least one phosphono radical are bonded to such carbon atoms through the sulfur atom and the phosphorus atom, respectively. These compounds are preferably non-polymeric; that is, they have a molecular weight of about 5000 or less. These sulfonic acids may be represented by compounds selected from the group of compounds represented by the general formula:

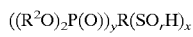

wherein R is an organo radical having at least one covalent carbon-fluorine bond; $R^2$ is hydrogen or a hydrocarbyl radical having up to 20 carbon atoms, for example, a lower alkyl radical; r is 2 or 3, preferably 3; y is an integer of from 1 to 3; and x is an integer of from 1 to 3, with the proviso that the phosphorus and the sulfur are covalently bonded to a carbon atom.

In another embodiment, the above fluorinated phosphonosulfonic acids may be reacted with a tetravalent metal ion to provide a solid acid having pendant sulfonic acid groups, according to the procedures described in the U.S. Pat. Nos. 4,232,146; 4,235,990; 4,235,991; 4,256,872; 4,267,308; 4,276,409; 4,276,410; 4,276,411; 4,298,723; 4,299,943; 4,373,079; 4,384,981; 4,386,013; 4,390,690; 4,429,111 and 4,436,899. In this embodiment, the phosphonic acid derivative (that is, $R^2$ is hydrogen) is reacted with a tetravalent metal ion to yield a solid compound represented by the general formula:

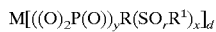

wherein M is the tetravalent metal; and d is ⅔, 1 or 2, as y varies from 3 to 2 to 1, respectively.

In another embodiment, the sulfonic acid may be prepared by the sulfonation of the reaction product of a tetravalent metal ion and $(R^2O)_2P(O)_yR^7$, wherein $R^2$ and y are as defined above, and $R^7$ is an organo radical having at least one covalent carbon-fluorine bond and at least one sulfonatable group, for example, an aryl or olefin group.

Finally, the sulfonic acid may be prepared by sequential impregnation of the tetravalent metal ion and $((HO)_2P(O))_yR(SO_rR^1)_x$ onto a suitable support e.g., a refractory inorganic oxide such as silicon oxide, and reacting the impregnated support to yield a supported $M[((O)_2P(O))_yR(SO_rR^1)_x]_d$.

The catalyst complex described in U.S. Pat. No. 5,414,187 uses one or more Lewis acids in conjunction with the organosulfonic acid or acid derivative described in U.S. Pat. No. 5,414,187 and in PCT application WO 90/07480. A Lewis acid is a molecule which can form another ion by forming a complex in which it accepts two electrons from a second molecule or ion. Typical strong Lewis acids include boron halides such as $BF_3$, $BCl_3$, $BBr_3$ and $BI_3$; antimony pentachloride ($SbF_5$); aluminum halides ($AlCl_3$ and $AlBr_3$); titanium halides such as $TiBr_4$, $TiCl_4$ and $TiCl_3$; zirconium tetrachloride ($ZrCl_4$); phosphorus pentafluoride ($PF_5$); iron halides such as $FeCl_3$ and $FeBr_3$, and the like. Weaker Lewis acids such as tin, indium, bismuth, zinc, or mercury halides are also acceptable. Preferred Lewis acids are $SbF_5$, $AlCl_3$ and $BF_3$; most preferred is $BF_3$.

In addition, as disclosed in aforesaid U.S. Pat. No. 3,887,635, the halosulfuric acid or halosulfonic acid or both can be used in admixture with one or more moderators as the alkylation catalyst system. The term "moderator" as used therein is defined as a compound which, in combination with a strong acid, produces a catalyst system of reduced activity vis-a-vis the strong acid, and thereby decreases the probability of competing side reactions, such as polymerization, which have a detrimental effect on product quality, while increasing catalyst selectivity, resulting in high quality alkylate product. Suitable moderators generally contain at least one oxygen atom per molecule and include water, aliphatic and cycloaliphatic alcohols and ethers, aliphatic, cycloaliphatic and aromatic sulfonic and carboxylic acids and their derivatives and inorganic acids.

Suitable contact materials for use in the method of the present invention include any porous solid that is able to form an adduct with the acid alkylation catalyst and does not react or disintegrate under alkylation conditions. Thus, suitable materials include any of the non-basic materials with polar surface groups and with sufficient adsorption capacity for the acid catalyst relative to that for the hydrocarbons in the reaction and product streams to provide high adsorption rates during passage of the acid catalyst-containing product stream through the contact material. Preferably the support material comprises a solid material with a Hammett acidity $H_0>-8$ calculated on the material in protonated form. Thus, preferred materials are silica, alumina, zirconia, titania, niobium oxide, tin oxides or mixtures thereof. Other suitable materials include polymer resins with pyridine groups, amine groups, other basic groups, or porous forms of carbon including forms of activated carbon. Of these, preferred materials are protonated forms of polyvinyl pyridine crosslinked with divinyl benzene and/or polystyrene amines.

In the method of the present invention, the catalytic alkylation process is carried out in each alkylation reactor at a temperature in the range of from about −30° C., preferably from about −15° C., more preferably from about 0° C., to about 100° C., preferably to about 50° C., more preferably to about 15° C. Higher temperatures tend to produce larger amounts of polymeric products and a reduced octane alkylate.

In the method of the present invention, the catalytic alkylation process is carried out in each alkylation reactor at a pressure in the range of from about 1 to about 100 atmospheres, depending on the composition of the process stream and the actual reaction temperature. Where the reaction is carried out at temperatures above about −10° C., it is necessary that the reaction be conducted under superatmospheric pressure, if both the reactants and catalyst are to be maintained substantially in the liquid state. Typically, the alkylation reaction is conducted at pressures varying from about 1 to 20 atmospheres. In general, it is preferable to use pressures sufficient to maintain the reactants in the liquid phase although a vapor phase operation is also contemplated. Autorefrigerative reactors and the like may be employed to maintain liquid phase operation. Although it is preferred to run the reaction neat, solvents or diluents may be employed, if desired.

The number of alkylation reactors, x, employed in the method of this invention is from 2, preferably from 3 to 20, preferably to 10. The fraction of the total amount of alkylating agent employed in the method of this invention that is introduced into each alkylation reactor in the series is $1/x\pm up$ to 0.3, preferably is $1/x\pm up$ to 0.2, more preferably is $1/x\pm up$ to 0.1, and most preferably is $1/x$.

For the present purposes, the fresh feed to any particular alkylation reactor employed in the method of the present invention, is the fresh alkylating agent and hydrocarbon substrate introduced into that reactor. Thus, the amount of hydrocarbon substrate that is recycled to that reactor and that is employed essentially as a refrigerant or diluent within the reactor for the fresh feed is not included in the calculation of the amount of fresh feed. The weight ratio, conventionally referred to as the external weight ratio in the alkylation art of the hydrocarbon substrate to alkylating agent in the fresh feed is in the range of from about 2, preferably from about 4, and more preferably from about 7, to about 100, preferably to about 20, and more preferably to about 12.

For the present purposes, the total feed to any particular alkylation reactor employed in the method of the present invention is the combination of the aforesaid fresh feed, and all the total amount of hydrocarbon substrate (and alkylating agent, if any) recycled to that reactor. Thus, any hydrocarbon substrate that is recycled to the reactor and employed essentially as a refrigerant or diluent within the reactor is included in the calculation of the amount of total feed. The weight ratio, conventionally referred to as the internal weight and recycled ratio in the alkylation art, of fresh hydrocarbon substrate to alkylating agent in the reactor is in the range of from about 4, preferably from about 10, and more preferably from about 20, to about 1000, preferably to about 100, and more preferably to about 30.

A number of alternatives are available in the method of the present invention for directing the product stream that comprises alkylation products and unreacted hydrocarbon substrate and that is withdrawn from a particular reactor. In one alternative, the entire such product stream is transferred to the next reactor in the series, and optionally at least a portion of the alkylation product is removed from the stream before it is introduced into the next reactor. In addition to or instead of removing alkylation product, a lower boiling inert such as propane can be removed from the product stream at this point. In another alternative, one portion of the product stream is recycled to the reactor from which it was withdrawn and a second portion of the product stream is transferred to the next reactor in the series, optionally after at least a portion of the alkylation product is removed from such second portion.

Furthermore, when the acid catalyst has migrated completely through the packed bed of particulate contact material to the outlet of the particular alkylation reactor, a significant portion of the acid catalyst enters the product stream as an additional component of it. Then, in one alternative, the catalyst is separated from the product stream before the product stream is passed to the next alkylation reactor in the series, before alkylation product (and/or inert material) is optionally removed from the product stream and before a portion of the product stream is recycled to the reactor from which it was withdrawn and a second portion is passed to the next alkylation reactor in the series.

Two preferred embodiments of the method of this invention are illustrated schematically in FIGS. 1 and 2. While the alkylation can be conducted in from 2 to 20 alkylation reactors in series in the method of this invention, for the sake of simplicity FIGS. 1 and 2 illustrate embodiments that contain only two alkylation reactors in series.

It also must be pointed out that FIGS. 1 and 2 are schematic representations and therefore that various features such as heat exchangers, pumps and valves, which are conventional parts of a process plant, are not shown in FIGS. 1 and 2. Various alternatives and additional process steps, such as addition of the acid catalyst to the alkylation reactor, recovery of the acid catalyst from the alkylation reactor, and, if any, regeneration of the acid catalyst are also not shown.

Turning now to FIGS. 1 and 2, one preferred embodiment of the method of this invention is shown in FIG. 1. A fresh supply of a suitable hydrocarbon substrate is introduced through line 5 and combined in line 6 with a recycle stream of hydrocarbon substrate (from line 53), and the resulting stream is combined with a suitable alkylating agent from line 7. The resulting mixture of the hydrocarbon substrate and the alkylating agent is then combined with a recycle stream of alkylate product and unreacted hydrocarbon substrate (from line 22) and the combination is introduced as the process stream through line 8 into the reactor 10 which contains a fixed bed 11 of a suitable particulate contact material 12.

A suitable halogenated sulfuric acid or halogenated sulfonic acid alkylation catalyst is previously deposited on the surface of a confined volume 13 of particulate contact material at the top of bed 11. The acid catalyst is adsorbed strongly on the contact material that constitutes the reaction zone 14, and only traces exit from the reactor 10 in the product stream through the line 15. The reaction zone 14 is shown at the middle of the bed 11 of contact material 12 in the reactor 10. The band width of adsorbed acid within the reaction zone 14 is determined by the number of theoretical plates and the capacity of the contact material 12 used. Within the reaction zone 14, the process stream is converted at alkylation conditions to a product stream containing alkylated products and unreacted hydrocarbon substrate and, if any, unreacted alkylating agent. Because of the high rate of the alkylation reaction under typical alkylation conditions and the high ratio of hydrocarbon substrate to alkylating agent in the process stream, generally there is essentially no unreacted alkylating agent in the product stream leaving the reactor 10 through the line 15.

During the alkylation reaction, the acid catalyst and, consequently, the reaction zone 14 continually move downward to new positions within the bed 11 located nearer the outlet end of the reactor 10 by interaction of the acid catalyst with the process stream and product stream flowing downward through the bed 11. The migration speed of the acid catalyst (and hence the reaction zone 14) in the bed 11 in the reactor 10 is lower than the migration speed of the hydrocarbons in the process and product streams through the bed 11, resulting in a very long elution time for the acid catalyst compared to the elution time for the hydrocarbons, during which time the activity of the acid catalyst is substantially retained, and the acid is still catalytically active when the catalyst (and the reaction zone 14) reaches the outlet of the reactor 10. The reaction zone 14 is shown at approximately the middle of the bed 11 of contact material 12 in the reactor 10.

When the reaction zone 14 reaches or nears the bottom of the reactor 10, another batch of acid catalyst is introduced into the confined volume 13 of the particulate contact material 12 at the top of the bed 11 of contact material 12 within the reactor 10, from which it also continually moves downward, as described hereinabove. When the acid catalyst exits from the reactor 10 through the line 15 in the product stream, the acid catalyst is separated in the separator 16 from the product stream.

The product stream passes from the reactor 10 in the line 15 to the separator 16 where acid catalyst is separated from the product stream. Any conventional convenient separation device or system can be employed as separator 16. One suitable system is a liquid-liquid decanter. The resulting substantially catalyst-free product stream then passes in line 17 and the separated acid catalyst passes through the line 18 for recovery and ultimately reintroduction into the alkylation reactor, optionally after regeneration. The product stream in line 17 is then split into a recycle stream which is returned to the reactor 10 through the lines 22 and 8 and a second stream which is passed in line 23 and is combined with additional alkylating agent from line 35. The resulting mixture is then combined with a recycle stream of alkylate product and unreacted hydrocarbon substrate (from line 49), and the combination is introduced as the second process stream which is introduced through the line 36 into the second alkylation reactor 37.

Within reactor 37, a suitable halogenated sulfuric acid or halogenated sulfonic acid alkylation catalyst is previously deposited on the surface of a confined volume 40 of particulate contact material 39 at the top of the bed 38. The acid catalyst is adsorbed strongly on the contact material that constitutes the reaction zone 41. The adsorption, band width and movement of the reaction zone 41 within the fixed bed 38 in the reactor 37 are as described hereinabove for the reaction zone 14 in the reactor 10. The reaction zone 41 is shown at the bottom of the bed 38 of contact material 39 in the reactor 37.

The product stream passes from the reactor 37 in the line 42 to the separator 43 where acid catalyst is separated from the product stream. Any convenient conventional separation device or system can be employed as the separator 43. One suitable system is a liquid-liquid decanter.

The resulting substantially catalyst-free product stream then passes in line 44 and the separated acid catalyst passes through the line 45 for recovery and ultimately reintroduction into the alkylation reactor, optionally after regeneration. The product stream in line 44 is then split into a recycle stream which is then returned to the reactor 37 through the lines 49 and 36 and a second stream which is passed in line 50 to a separation system 51, where alkylation product is separated from unreacted hydrocarbon substrate and recovered through line 52. The unreacted hydrocarbon substrate is withdrawn from the separation system 51 and recycled to the first reactor 10 through the lines 53, 6 and 8.

When the reaction zone 41 reaches or nears the bottom of the reactor 37, another batch of acid catalyst is introduced into a confined volume 40 of the particulate contact material 39 at the top of the bed 38 within the reactor 37, from which it also continually moves downward, as described hereinabove.

Another preferred embodiment of the method of this invention is shown in FIG. 2. Elements in the embodiment of FIG. 2 that correspond to elements in the embodiment of FIG. 1 are numbered the same as the corresponding elements in the embodiment of FIG. 1. Elements in the embodiment of FIG. 2 which function as do corresponding elements in the embodiment of FIG. 1 will not be described further. The sole difference between the embodiments of FIGS. 1 and 2 is that instead of the product stream being passed from the first reactor 10 to the second reactor 37 through the lines 17, 23 and 36 as in the embodiment of FIG. 1, in the embodiment of FIG. 2 the product stream is conducted in line 17 from the first reactor 10 to a separation zone 19 where, as in separation zone 51 in FIG. 1, at least a portion of the alkylate and/or diluents such as propane are removed from the product stream and recovered through the line 20 (and additional lines, if necessary) and the remainder of the product stream from reactor 10 (that is not recycled to reactor 10 through line 22) is then conducted through line 21 to line 23 and is then combined with alkylating agent from line 35 and recycle from line 49 to form the process stream which passes through the line 36 into the second reactor 37.

Thus, as illustrated by the embodiments of FIGS. 1 and 2, the method of the present invention permits the use in the different alkylation reactors employed of the same or different alkylating agents, the same or different acid catalysts, the same or different contact materials, the same or different weight ratios of hydrocarbon substrate to alkylating agent, the same or different weight ratios of acid catalyst to alkylating agent, and the same or different alkylation conditions. As a result, the same or different alkylate products can be formed in the different alkylation reactors employed.

Thus, the alkylation conditions in each reactor can be optimized for the formation and stability of the particular alkylation product formed in each such reactor. Each of FIGS. 1 and 2 illustrates that, if different acid catalysts are employed in different alkylation reactors, the catalysts can be recovered separately, through lines 18 and 45, and thus mixing thereof is eliminated. In addition, if different alkylation products are formed in the different reactors, FIG. 2 illustrates that the different alkylation products can be recovered separately without the need to subsequently separate one product from the other. On the other hand, if there is no need or desire to separate the various different alkylation products, FIG. 1 illustrates that the different alkylation products can be recovered together. FIGS. 1 and 2 further illustrate that recycle to each reactor can be independently optimized to maximize the selectivity of the alkylation reaction in each such reactor.

EXAMPLES 1–3

The staged alkylation in Examples 1 and 2 are performed using a configuration of alkylation reactors and recycle to each alkylation reactor as shown in FIGS. 1 and 2, respectively. In each of Examples 1 and 2, two alkylation reactors in series are employed in the staged alkylation. In Example 3, ten alkylation reactors in series are employed in the staged alkylation using a configuration of alkylation reactors as shown in FIG. 1, but without any recycle of effluent through lines 22 and 49. In the staged alkylation in each of Examples 1 and 2, for each alkylation reactor, the product stream is withdrawn from the reactor and about 66–69 weight percent of the product stream is recycled, for example, through lines 22 or 49, to the alkylation reactor from which it was withdrawn. The remaining about 31–34 weight percent of the product stream for each such alkylation reactor, except the last one in the series, is transferred, for example, through the lines 23 and 36, to the next alkylation reactor in the series, and for the last reactor in the series is withdrawn, for example, through line 52, as alkylate product. In the staged alkylation of Example 2, about 6 weight percent of the product stream withdrawn from reactor 10 and reactor 37 in lines 17 and 44 are flashed in separator 19 or separator 46, respectively, and the remainder of the product stream is split with about 69% in lines 22 and 49, respectively, and 31% in lines 23 and 50, respectively.

In each of Examples 1–2, a comparison is made of the aforesaid staged alkylation in two reactors in series versus unstaged alkylation in only one reactor, at an equal isobutane recycle (through line 53) and equal effluent recycle (through line 22). For such unstaged alkylation, by reference to FIG. 1, the fraction of the product stream from the sole reactor withdrawn from the separator 19 is collected for recovery of the alkylate product rather than being transferred to another alkylation reactor.

In each of Examples 1 and 2, 100 weight percent of the total amount of fresh (not recycled) olefin, isoparaffin and diluent is added to the sole reactor in the unstaged case, while 50 weight percent is added to each of the two reactors employed in the staged case. In Example 3, 100 weight percent of the total amount of fresh (not recycled) olefin, isoparaffin and diluent is added to the sole reactor in the unstaged case, while 10 weight percent is added to each of the ten reactors employed in the staged case, but no effluent is recycled.

The compositions in weight percent of (a) the Fresh Feed—that is, unrecycled olefin, isoparaffin and diluent (added through lines 5, 7 and 35 in FIGS. 1 and 2)—(b) Total Feed—that is, the Fresh Feed plus materials recycled to the reactor in question (added through lines 8 and 36 in FIGS. 1 and 2), and (c) the Total Reactor Effluent from such reactor (in lines 17 and 44 in FIGS. 1 and 2) for Examples 1–3 are presented in Tables 1–3, respectively. Also shown in Tables 1–3 are the temperatures at which the Total Feed to a particular reactor is introduced into such reactor and at which the Total Reactor Effluent is withdrawn from such reactor.

The data in Table 1 illustrates that, measured from the Total Feed temperature of 75° F., the average temperature increase in the two alkylation reactors in the staged case is almost 19° F. less than in the sole reactor for the unstaged case. Furthermore, the average concentrations of olefin and alkylate product in the Total Feed to the two alkylation reactors in the staged case is about 1.62 weight percent less and about 2.09 weight percent less, respectively, and the average isoparaffin concentration in the Total Feed to the two alkylation reactors in the staged case is about 3.47 weight percent higher, than in the unstaged case. Based on this, it is calculated that the final alkylate product from the staged case has an octane number of about 2.2 higher than the alkylate product from the unstaged case.

The data in Table 2 illustrates that, measured from the Total Feed temperature of 50° F., the average temperature increase in the two alkylation reactors in the staged case is more than 15° F. less than in the sole reactor for the unstaged case. Furthermore, the average concentrations of olefin and alkylate product in the Total Feed to the two alkylation reactors in the staged case is about 1.34 weight percent less and about 9.38 weight percent less, respectively, and the average isoparaffin concentration in the Total Feed to the two alkylation reactors in the staged case is about 10.34 weight percent higher, than in the unstaged case. Based on this, it is calculated that the final alkylate product from the staged case has an octane number of about 2.9 higher than the alkylate product from the unstaged case.

The data in Table 3 illustrates that, measured from the Total Feed temperature of 75° F., the average temperature increase in the ten alkylation reactors in the staged case is about 26° F. less than in the sole reactor for the unstaged case. Furthermore, the average concentrations of olefin and alkylate product in the Total Feed to the ten alkylation reactors in the staged case is about 2.2 weight percent less and about 4.8 weight percent less, respectively, and the average isoparaffin concentration in the Total Feed to the ten alkylation reactors in the staged case is about 6.6 weight percent higher, than in the unstaged case. Based on this, it is calculated that the final alkylate product from the staged case has an octane number of about 3.2 higher than the alkylate product from the unstaged case.

From the above description, it is apparent that the objects of the present invention have been achieved. While only certain embodiments and various modifications have been described, numerous alternative embodiments and various modifications will be apparent from the above description to those skilled in the art. These alternatives and embodiments are considered equivalents and within the spirit and scope of the present invention.

TABLE 1

| Components | Composition (Vol. %) | | | | | | | | |
|---|---|---|---|---|---|---|---|---|---|
| | Fresh Feed | Fresh Feed and Recycle | Total Reactor Effluent | Fresh Feed | Fresh Feed and Recycle | Total Reactor Effluent | Fresh Feed | Fresh Feed and Recycle | Total Reactor Effluent |
| UNSTAGED | | Reactor No. 1 | | | | | | | |
| Olefin | 38 | 3.26 | 0 | | | | | | |
| Alkylate | 0 | 12.29 | 18 | | | | | | |
| Isoparaffin | 46 | 65 | 62 | | | | | | |
| Diluent | 15 | 19 | 20 | | | | | | |
| Temperature (°F.) | | 75 | 112 | | | | | | |
| Percent of effluent recycled | | | 66 | | | | | | |
| STAGED | | Reactor No. 1 | | | Reactor No. 2 | | | Average Of Both Reactors | |
| Olefin | 38 | 1.72 | 0 | 38 | 1.55 | 0 | | 1.63 | |
| Alkylate | 0 | 6.39 | 9 | 0 | 14.02 | 17 | | 10.20 | |
| Isoparaffin | 46 | 72 | 67 | 46 | 65 | 64 | | 69 | |
| Diluent | 15 | 20 | 19 | 15 | 19 | 20 | | | |

TABLE 1-continued

Composition (Vol. %)

| Components | Fresh Feed | Fresh Feed and Recycle | Total Reactor Effluent | Fresh Feed | Fresh Feed and Recycle | Total Reactor Effluent | Fresh Feed | Fresh Feed and Recycle | Total Reactor Effluent |
|---|---|---|---|---|---|---|---|---|---|
| Temperature (°F.) | | 75 | 95 | | 75 | 93 | | 75 | 93.7 |
| Percent of effluent recycled | | | 69 | | | 69 | | | 69 |

TABLE 2

Composition (Vol. %)

| Components | Fresh Feed | Fresh Feed and Recycle | Total Reactor Effluent | Fresh Feed | Fresh Feed and Recycle | Total Reactor Effluent | Fresh Feed | Fresh Feed and Recycle | Total Reactor Effluent |
|---|---|---|---|---|---|---|---|---|---|
| UNSTAGED | | Reactor No. 1 | | | | | | | |
| Olefin | 38 | 2.47 | 0 | | | | | | |
| Alkylate | 0 | 29.07 | 34 | | | | | | |
| Isoparaffin | 46 | 49 | 47 | | | | | | |
| Diluent | 15 | 15 | 19 | | | | | | |
| Temperature (°F.) | | 50 | 78 | | | | | | |
| Percent of effluent recycled | | | 67 | | | | | | |
| STAGED | | Reactor No. 1 | | | Reactor No. 2 | | | Average of Both Reactors | |
| Olefin | 38 | 1.31 | 0 | 38 | 0.95 | 0 | | 1.13 | |
| Alkylate | 0 | 9.81 | 11 | 0 | 29.58 | 31 | | 19.69 | |
| Isoparaffin | 46 | 69 | 65 | 46 | 50 | 49 | | 60 | |
| Diluent | 15 | 20 | 19 | 0 | 19 | 19 | | | |
| Temperature (°F.) | | 50 | 65 | | 50 | 61 | | | 62.9 |
| Percent of effluent recycled | | | 69 | | | 69 | | | |

TABLE 3

Composition (Vol. %)

| Components | Fresh Feed | Fresh Feed and Recycle | Total Reactor Effluent | Fresh Feed | Fresh Feed and Recycle | Total Reactor Effluent | Fresh Feed | Fresh Feed and Recycle | Total Reactor Effluent |
|---|---|---|---|---|---|---|---|---|---|
| UNSTAGED | | Reactor No. 1 | | | | | | | |
| Olefin | 38 | 3.26 | 0 | | | | | | |
| Alkylate | 0 | 12.29 | 18 | | | | | | |
| Isoparaffin | 46 | 65 | 64 | | | | | | |
| Diluent | 15 | 19 | 20 | | | | | | |
| Temperature (°F.) | | 75 | 112 | | | | | | |
| Percent of effluent recycled | | | 70 | | | | | | |
| STAGED | | Reactor No. 1 | | | Reactor No. 2 | | | Reactor No. 3 | |
| Olefin | 38 | 1 | 0 | 38 | 1 | 0 | 38 | 1 | 0 |
| Alkylate | 0 | 0 | 2 | 0 | 2 | 4 | 0 | 4 | 6 |
| Isoparaffin | 46 | 79 | 78 | 46 | 77 | 76 | 46 | 76 | 75 |
| Diluent | 15 | 20 | 20 | 15 | 20 | 20 | 15 | 20 | 20 |
| Temperature (°F.) | | 75 | 88 | | 75 | 80 | | 75 | 88 |
| Percent of effluent recycled | | | 0 | | | 0 | | | 0 |
| | | Reactor No. 4 | | | Reactor No. 5 | | | Reactor No. 6 | |
| Olefin | 38 | 1 | 0 | 38 | 1 | 0 | 38 | 1 | 0 |
| Alkylate | 0 | 5 | 7 | 0 | 7 | 9 | 0 | 9 | 10 |
| Isoparaffin | 46 | 74 | 73 | 46 | 72 | 71 | 46 | 71 | 70 |
| Diluent | 15 | 20 | 20 | 15 | 20 | 20 | 15 | 20 | 20 |
| Temperature (°F.) | | 75 | 87 | | 75 | 87 | | 75 | 86 |
| Percent of effluent recycled | | | 0 | | | 0 | | | 0 |

TABLE 3-continued

| Components | Composition (Vol. %) | | | | | | | | |
|---|---|---|---|---|---|---|---|---|---|
| | Fresh Feed | Fresh Feed and Recycle | Total Reactor Effluent | Fresh Feed | Fresh Feed and Recycle | Total Reactor Effluent | Fresh Feed | Fresh Feed and Recycle | Total Reactor Effluent |
| | Reactor No. 7 | | | Reactor No. 8 | | | Reactor No. 9 | | |
| Olefin | 38 | 1 | 0 | 38 | 1 | 0 | 38 | 1 | 0 |
| Alkylate | 0 | 10 | 12 | 0 | 12 | 13 | 0 | 13 | 15 |
| Isoparaffin | 46 | 69 | 68 | 46 | 68 | 67 | 46 | 67 | 66 |
| Diluent | 15 | 20 | 20 | 15 | 20 | 20 | 15 | 20 | 20 |
| Temperature (°F.) | | 75 | 86 | | 75 | 86 | | 75 | 86 |
| Percent of effluent recycled | | | 0 | | | 0 | | | 0 |
| | Reactor No. 10 | | | Average Of Ten Reactors | | | | | |
| Olefin | 38 | 1 | 0 | | 1.02 | | | | |
| Alkylate | 0 | 14 | 16 | | 7.52 | | | | |
| Isoparaffin | 46 | 65 | 65 | | 72 | | | | |
| Diluent | 15 | 20 | 20 | | | | | | |
| Temperature (°F.) | | 75 | 86 | | 75 | 87 | | | |
| Percent of effluent recycled | | | 0 | | | | | | |

I claim:

1. In a process for the liquid phase alkylation of a hydrocarbon substrate which is comprised of paraffins with an olefinic alkylating agent in the presence of a halogenated sulfuric acid or halogenated sulfonic acid catalyst in a fixed bed of particulate contact material in an alkylation reactor, comprising the steps of establishing on the contact material a reaction zone of the halogenated sulfuric acid or halogenated sulfonic acid catalyst adsorbed on a confined volume of the contact material within the fixed bed, passing a process stream of the hydrocarbon substrate and alkylating agent at alkylation conditions in one flow direction through the reactor, with the acid catalyst and reaction zone migrating on the contact material in the fixed bed in the direction of flow of the process stream and at a relatively lower superficial velocity than the superficial velocity of the process stream and product stream comprising alkylated products and unreacted hydrocarbon substrate, and withdrawing the product stream from the reactor, the improvement comprising:

(a) staging the alkylation reaction by simultaneously reacting a portion of said substrate with a portion of said alkylating agent in each of x alkylation reactors which are connected in series, wherein x is from 2 to 20, and introducing into each such reactor a fraction of $1/x \pm$ up to 0.3 of the total amount of at least one alkylating agent employed, with the fraction introduced into one such reactor being the same as or different from the fraction introduced into any other such reactor in the series, with the contact material and catalyst employed in one such reactor being the same as or different from the contact material and catalyst, respectively, employed in any other such reactor, and with the alkylating agent and alkylation conditions employed in one such reactor being the same as or different from the alkylating agent and alkylation conditions, respectively, employed in any other such reactor;

(b) establishing on the contact material within the fixed bed in each such alkylation reactor a reaction zone with the acid catalyst adsorbed on a confined volume of such contact material;

(c) passing a process stream of aforesaid hydrocarbon substrate and an aforesaid fraction of aforesaid at least one alkylating agent at alkylation conditions in one flow direction through the first aforesaid alkylation reactor;

(d) withdrawing a product stream of alkylation products and unreacted hydrocarbon substrate from the first alkylation reactor;

(e) introducing into the next alkylation reactor in the series a process stream comprising at least a portion of the product stream of alkylation products and unreacted hydrocarbon substrate withdrawn from the preceding alkylation reactor in the series and another aforesaid fraction of aforesaid at least one alkylating agent, passing such process stream at alkylation conditions in one flow direction through such next alkylation reactor in the series, and withdrawing a product stream of alkylation products and unreacted hydrocarbon substrate from such next alkylation reactor; and (f) if x is greater than 2, repeating step (e) for each successive alkylation reactor in the series.

2. The process of claim 1 wherein two alkylation reactors in series are employed.

3. The process of claim 2 wherein $50 \pm$ up to 10 percent by weight of the total amount of aforesaid at least one alkylating agent employed in the alkylation reaction is introduced into each of the alkylation reactors in the series.

4. The process of claim 3 wherein substantially equal percents by weight of the total amount of aforesaid at least one alkylating agent employed in the alkylation reaction are introduced into each of the alkylation reactors in the series.

5. The process of claim 1 wherein substantially the entire product stream withdrawn from the first alkylation reactor is introduced into the second alkylation reactor in the series.

6. The process of claim 1 wherein acid catalyst in the product stream withdrawn from the first alkylation reactor is separated from the product stream before the product stream is introduced into the second alkylation reactor.

7. The process of claim 1 wherein the alkylation temperature in one alkylation reactor is different from the alkylation temperature in the next alkylation reactor in the series.

8. The process of claim 1 wherein the weight ratio of hydrocarbon substrate and alkylating agent in one alkylation reactor is different from the aforesaid weight ratio in the next alkylation reactor in the series.

9. The process of claim 1 wherein the weight ratio of acid catalyst to alkylating agent in the one alkylation reactor is different from the aforesaid weight ratio in the next alkylation reactor in the series.

10. The process of claim 1 wherein the alkylating agent employed in one alkylation reactor is different from the alkylating agent employed in the next alkylation reactor in the series.

11. The process of claim 1 wherein the acid catalyst employed in the one alkylation reactor is different from acid catalyst employed in the next alkylation reactor in the series.

12. The process of claim 1 wherein the mass flux of alkylating agent in one alkylation reactor is different from the mass flux of alkylating agent in the next alkylation reactor in the series.

13. The process of claim 1 wherein said hydrocarbon substrate is comprised of hydrocarbons which are selected from the group consisting of straight and branched chain $C_2$ to $C_{10}$ paraffins.

14. The process of claim 1 wherein said hydrocarbon substrate is comprised of $C_4$ to $C_6$ isoparaffins.

15. The process of claim 1 wherein said catalyst is selected from the group consisting of $C_1$ to $C_4$ perfluorinated alkanesulfonic acids.

16. The process of claim 1 wherein said catalyst is selected from the group consisting of fluorosulfonic acid, trifluoromethanesulfonic acid and trifluoroethanesulfonic acid.

* * * * *